United States Patent
Pham et al.

(10) Patent No.: US 6,299,599 B1
(45) Date of Patent: Oct. 9, 2001

(54) DUAL BALLOON CENTRAL VENOUS LINE CATHETER TEMPERATURE CONTROL SYSTEM

(75) Inventors: Nora Tran Pham, Lake Forest; Lynn M. Shimada, Orange; Scott M. Evans, Santa Ana; Blair D. Walker, Mission Viejo, all of CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/427,745

(22) Filed: Oct. 27, 1999

Related U.S. Application Data

(63) Continuation-in-part of application No. 09/253,109, filed on Feb. 19, 1999.

(51) Int. Cl.⁷ ................................................ A61F 7/12
(52) U.S. Cl. .............. 604/113; 604/101.05; 604/101.03; 607/106
(58) Field of Search ................................. 604/113, 96.01, 604/101.01, 101.05, 101.03, 97.01, 99.01, 99.02; 607/96, 104, 105, 106

(56) References Cited

U.S. PATENT DOCUMENTS

| | | |
|---|---|---|
| Re. 32,983 | 7/1989 | Levy . |
| Re. 33,561 | 3/1991 | Levy . |
| Re. 35,352 * | 10/1996 | Peters ........................................ 604/4 |
| 2,308,484 | 1/1943 | Auzin et al. . |
| 3,125,096 | 3/1964 | Antiles et al. . |
| 3,142,158 | 7/1964 | Podolsky . |
| 3,238,944 | 3/1966 | Hirschhorn . |
| 3,282,267 | 11/1966 | Eidus . |
| 3,327,713 | 6/1967 | Eidus . |
| 3,425,419 | 2/1969 | Dato et al. . |
| 3,504,674 | 4/1970 | Swenson et al. . |
| 3,738,372 | 6/1973 | Shioshvili . |
| 3,776,241 | 12/1973 | Magilton . |
| 3,897,790 | 8/1975 | Magilton et al. . |
| 3,913,581 | 10/1975 | Ritson et al. . |
| 4,010,795 | 3/1977 | Stenberg . |
| 4,111,209 | 9/1978 | Wolvek et al. . |
| 4,154,245 | 5/1979 | Daily . |
| 4,249,923 | 2/1981 | Walda . |
| 4,298,006 | 11/1981 | Parks . |
| 4,416,280 | 11/1983 | Carpenter et al. . |
| 4,416,281 | 11/1983 | Cooper et al. . |
| 4,546,759 | 10/1985 | Solar . |
| 4,583,969 | 4/1986 | Mortensen . |
| 4,672,962 | 6/1987 | Hershenson . |
| 4,745,922 | 5/1988 | Taylor . |

(List continued on next page.)

FOREIGN PATENT DOCUMENTS

| | | |
|---|---|---|
| WO91/05528 | 5/1991 | (WO) . |
| WO98/31312 | 4/1998 | (WO) . |
| WO98/26831 | 6/1998 | (WO) . |

*Primary Examiner*—Anhtuan T. Nguyen
*Assistant Examiner*—Jeremy Thissell

(57) ABSTRACT

A system for controlling patient temperature uses a central venous line catheter having axially spaced distal and proximal heat exchange balloons. The central venous line catheter is provided with one or more lumens for providing access to the central blood supply of the patient, and with additional lumens for communicating heat exchange fluid to the balloons. Heat exchange fluid temperature is controlled through a feed back loop in which patient temperature is sensed and used to control a temperature control unit comprising a heating device and/or a cooling device in heat exchange relationship with the heat exchange fluid. A tubing set transports the heat exchange fluid between the central venous line and the temperature control unit, with a pump serving to circulate the fluid in a closed fluid circuit in the system.

30 Claims, 5 Drawing Sheets

U.S. PATENT DOCUMENTS

| | | |
|---|---|---|
| 4,748,979 | 6/1988 | Hershenson . |
| 4,750,493 | 6/1988 | Brader . |
| 4,754,752 | 7/1988 | Ginsburg et al. . |
| 4,759,349 | 7/1988 | Betz et al. . |
| 4,791,930 | 12/1988 | Suzuki et al. . |
| 4,813,210 | 3/1989 | Masuda et al. . |
| 4,823,076 | 4/1989 | Haines et al. . |
| 4,844,074 | 7/1989 | Kurucz . |
| 4,850,958 | 7/1989 | Berry et al. . |
| 4,860,744 | 8/1989 | Johnson et al. . |
| 4,883,455 | 11/1989 | Leonard . |
| 4,899,741 | 2/1990 | Bentley et al. . |
| 4,987,896 | 1/1991 | Nakamatsu . |
| 5,019,075 | 5/1991 | Spears et al. . |
| 5,021,045 | 6/1991 | Buckberg et al. . |
| 5,041,089 | 8/1991 | Mueller et al. . |
| 5,066,578 | 11/1991 | Wikman-Coffelt . |
| 5,078,713 | 1/1992 | Varney . |
| 5,092,841 | 3/1992 | Spears . |
| 5,098,376 | 3/1992 | Berry et al. . |
| 5,106,360 | 4/1992 | Ishiwara et al. . |
| 5,135,474 | 8/1992 | Swan et al. . |
| 5,139,496 | 8/1992 | Hed . |
| 5,147,355 | 9/1992 | Friedman et al. . |
| 5,147,385 | 9/1992 | Beck et al. . |
| 5,151,100 | 9/1992 | Abele et al. . |
| 5,158,534 | 10/1992 | Berry et al. . |
| 5,174,285 | 12/1992 | Fontenot . |
| 5,182,317 | 1/1993 | Winters et al. . |
| 5,191,883 | 3/1993 | Lennox et al. . |
| 5,196,024 | 3/1993 | Barath . |
| 5,211,631 | 5/1993 | Sheaff . |
| 5,230,862 | 7/1993 | Berry et al. . |
| 5,248,312 | 9/1993 | Langberg . |
| 5,250,070 | 10/1993 | Parodi . |
| 5,257,977 | 11/1993 | Eshel . |
| 5,259,839 | 11/1993 | Burns . |
| 5,261,399 | 11/1993 | Klatz et al. . |
| 5,262,451 | 11/1993 | Winters et al. . |
| 5,269,758 | 12/1993 | Taheri . |
| 5,275,595 | 1/1994 | Dobak, III . |
| 5,279,598 | 1/1994 | Sheaff . |
| 5,281,213 | 1/1994 | Milder et al. . |
| 5,281,215 | 1/1994 | Milder . |
| 5,304,214 * | 4/1994 | DeFord et al. ..................... 607/105 |
| 5,324,286 | 6/1994 | Fowle . |
| 5,338,770 | 8/1994 | Winters et al. . |
| 5,342,301 | 8/1994 | Saab . |
| 5,342,693 | 8/1994 | Winters et al. . |
| 5,354,277 | 10/1994 | Guzman et al. . |
| 5,370,616 | 12/1994 | Keith et al. . |
| 5,382,234 | 1/1995 | Cornelius et al. . |
| 5,411,477 | 5/1995 | Saab . |
| 5,423,744 * | 6/1995 | Gencheff et al. . |
| 5,423,807 | 6/1995 | Milder . |
| 5,437,673 | 8/1995 | Baust et al. . |
| 5,452,582 | 9/1995 | Longsworth . |
| 5,478,309 | 12/1995 | Sweezer et al. . |
| 5,486,204 | 1/1996 | Clifton . |
| 5,486,208 | 1/1996 | Gingsburg . |
| 5,531,776 | 7/1996 | Ward et al. . |
| 5,545,134 | 8/1996 | Hilaire et al. . |
| 5,545,137 | 8/1996 | Rudie et al. . |
| 5,545,161 | 8/1996 | Imran . |
| 5,549,552 | 8/1996 | Peters et al. . |
| 5,549,559 | 8/1996 | Eshel . |
| 5,562,606 | 10/1996 | Huybregts . |
| 5,588,965 * | 12/1996 | Burton et al. . |
| 5,599,307 * | 2/1997 | Bacher et al. ................. 604/101.05 |
| 5,609,620 | 3/1997 | Daily . |
| 5,624,392 | 4/1997 | Saab . |
| 5,655,548 | 8/1997 | Nelson et al. . |
| 5,656,420 | 8/1997 | Chien . |
| 5,693,080 | 12/1997 | Wallstéet al. . |
| 5,702,435 | 12/1997 | Maytal . |
| 5,716,386 | 2/1998 | Ward et al. . |
| 5,733,319 | 3/1998 | Neilson et al. . |
| 5,735,809 | 4/1998 | Gorsuch . |
| 5,758,505 | 6/1998 | Dobak, III et al. . |
| 5,759,182 | 6/1998 | Varney et al. . |
| 5,787,715 | 8/1998 | Dobak, III et al. . |
| 5,800,375 | 9/1998 | Sweezer et al. . |
| 5,837,003 | 11/1998 | Gungsburg . |
| 5,861,021 | 1/1999 | Thome et al. . |
| 5,865,789 * | 2/1999 | Hattler . |
| 5,879,329 | 3/1999 | Gingsburg . |
| 5,902,268 | 5/1999 | Saab . |
| 5,902,299 | 5/1999 | Jayaraman . |
| 5,906,588 | 5/1999 | Safar et al. . |
| 5,976,103 * | 11/1999 | Martin ................................ 604/284 |
| 6,126,684 * | 10/2000 | Gobin et al. . |

* cited by examiner

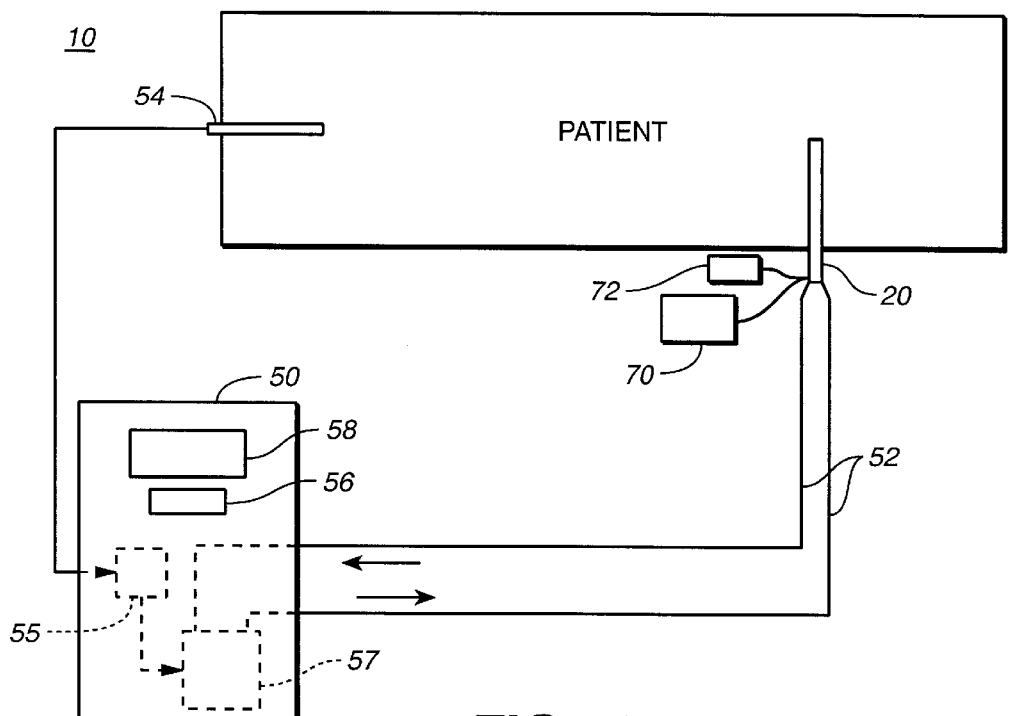
FIG._1
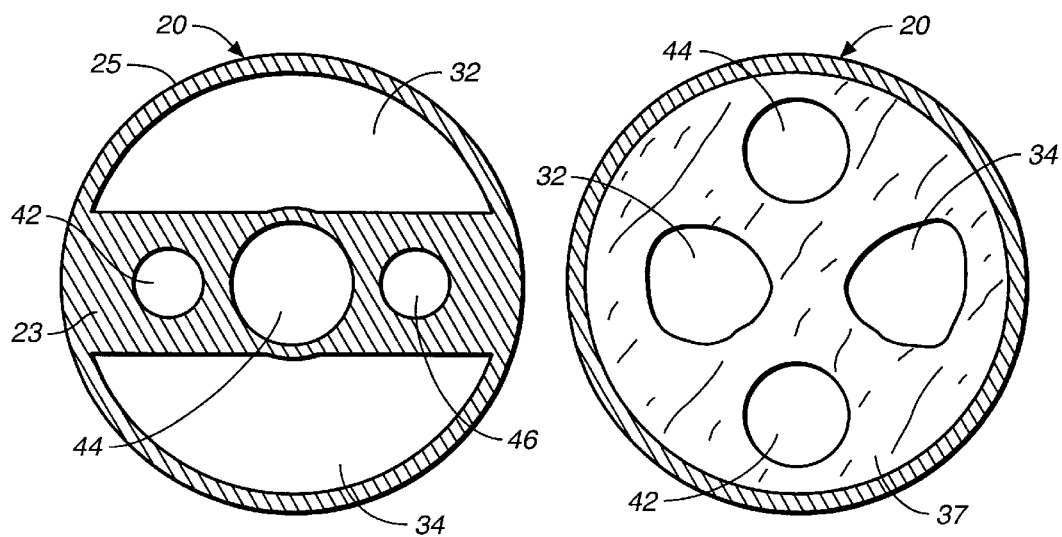
FIG._3  FIG._4

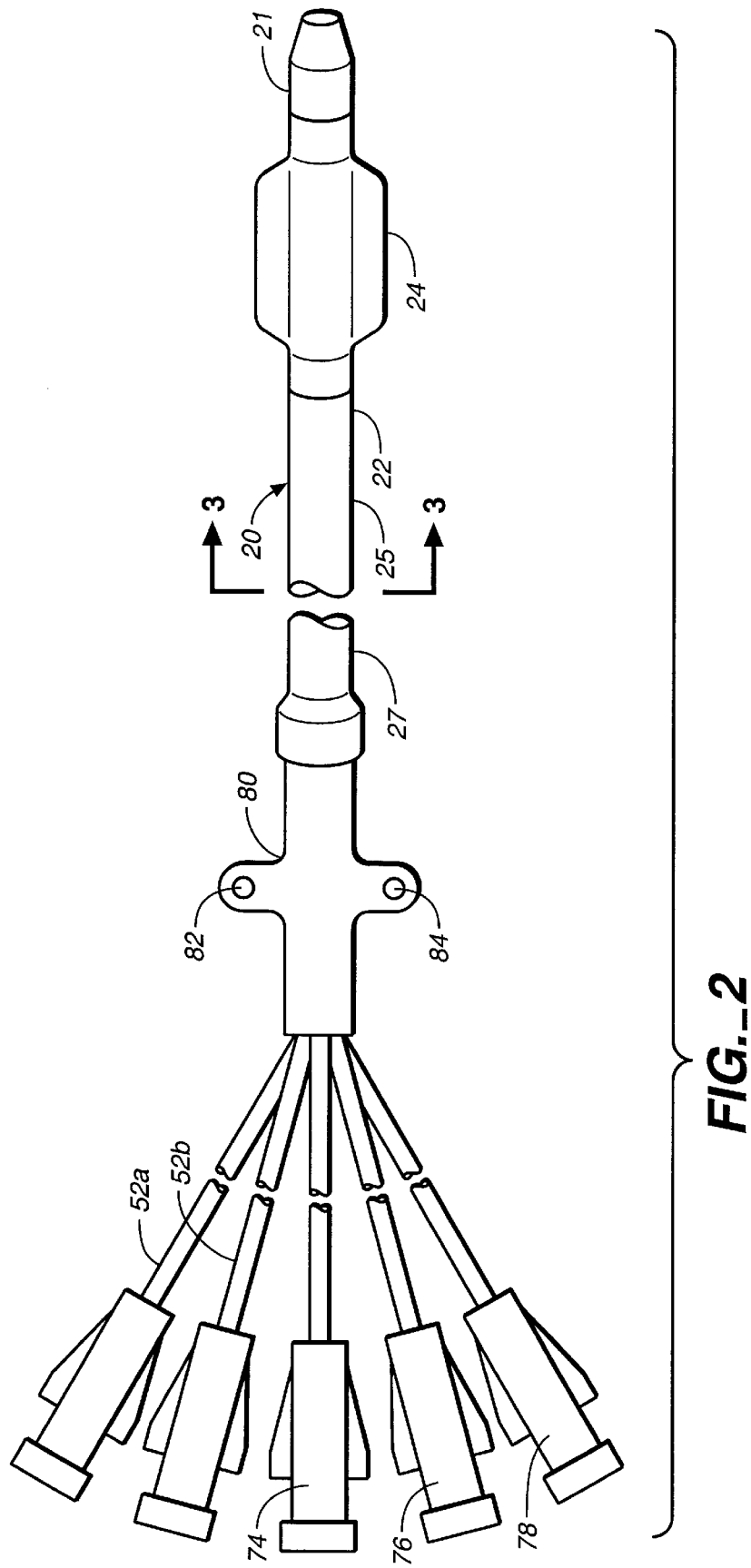
FIG._2

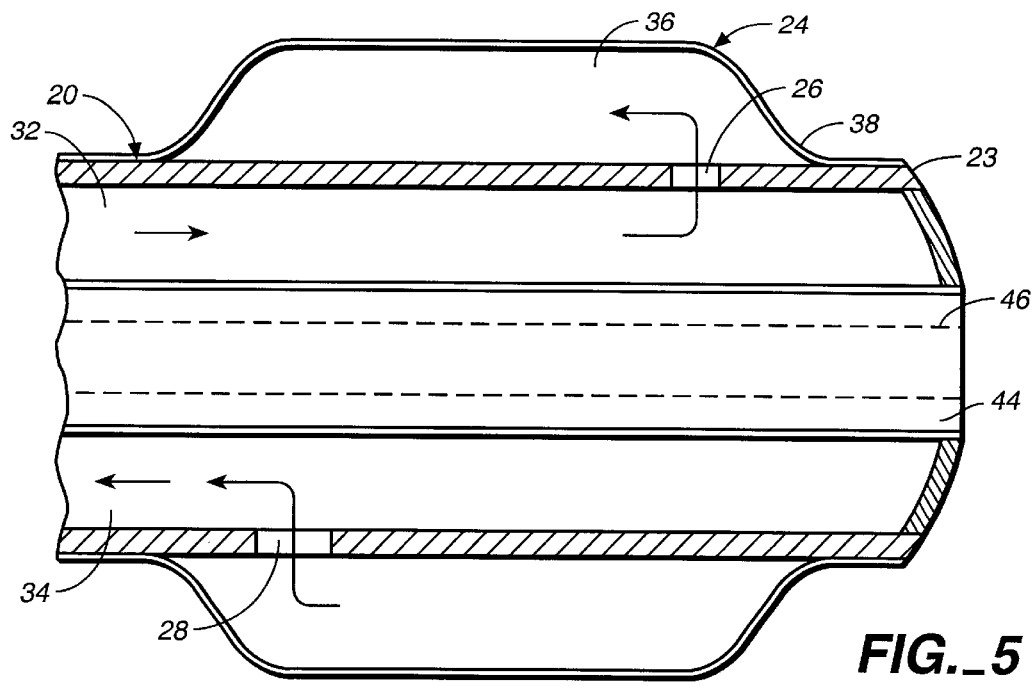
FIG._5
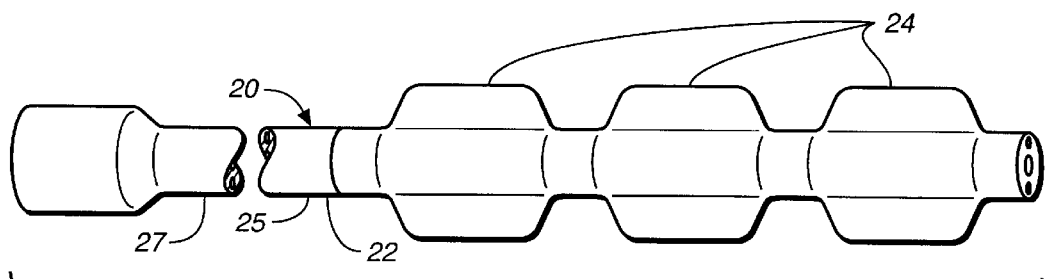
FIG._6
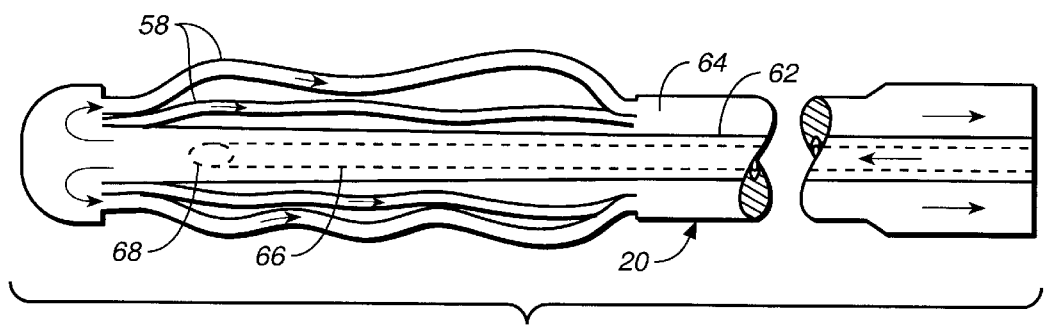
FIG._7

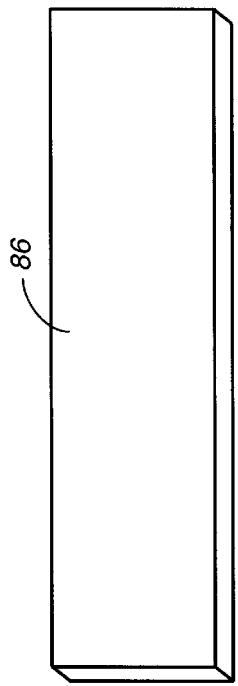
FIG._8
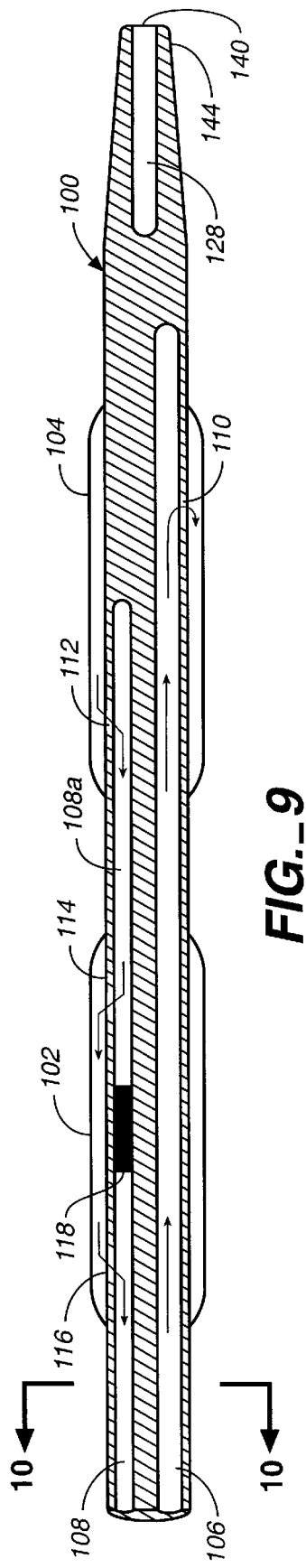
FIG._9
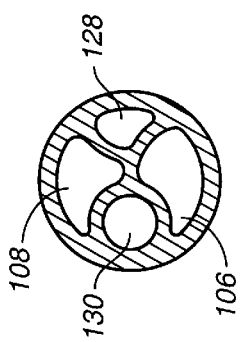
FIG._10

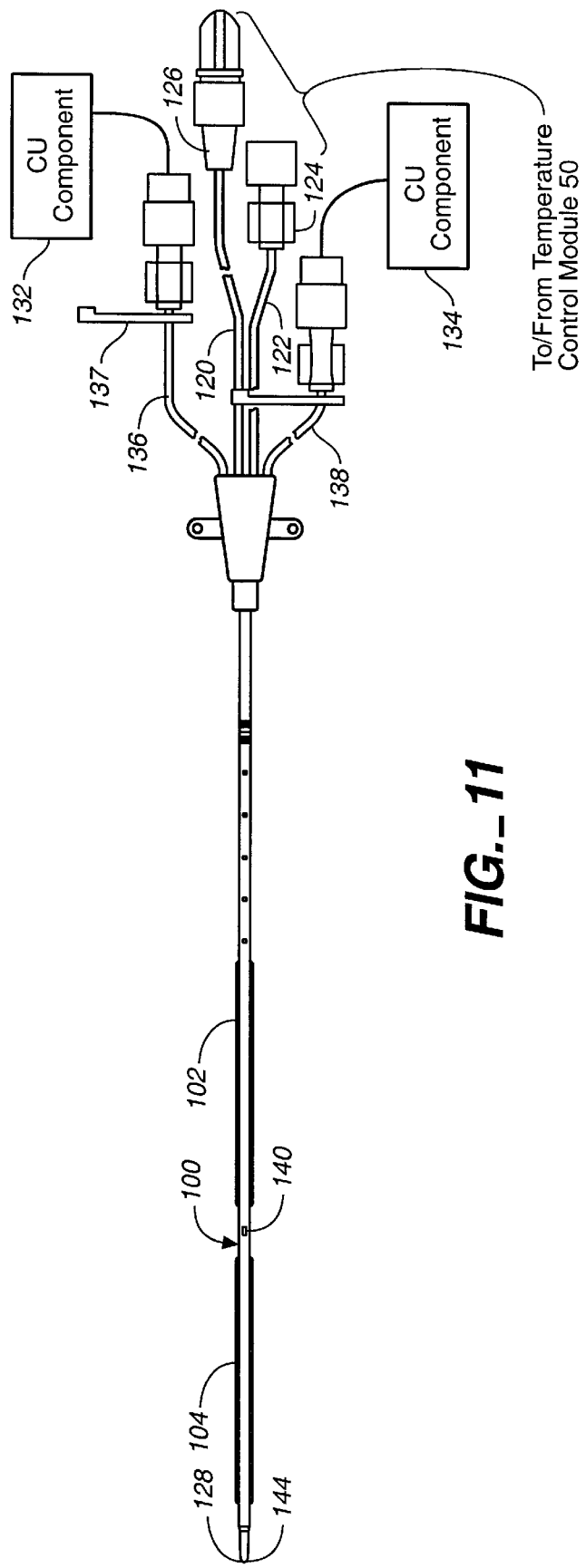
FIG._11

DUAL BALLOON CENTRAL VENOUS LINE CATHETER TEMPERATURE CONTROL SYSTEM

CROSS-REFERENCE TO RELATED APPLICATIONS

This application is a continuation-in-part (CIP) of U.S. patent application Ser. No. 09/253,109, filed Feb. 19, 1999.

BACKGROUND OF THE INVENTION

1. Field of the Invention

The invention relates to heat exchange catheters used for access to the central venous blood supply of a patient.

2. Description of Related Art

Catheters such as central venous catheters are typically used in ICU (intensive care unit) patients, particularly in those patients who have suffered a stroke or other brain traumatic event. The central venous line catheters are typically about 4–12 French in size and consist of a soft, flexible multi-lumen structure extending 8–12 inches. They are usually introduced through the subclavian or jugular vein, and some times in the femoral vein of the patient, serving to provide the caretaker with easy and convenient access to the patient's central blood supply via the central venous system. In this manner general access to the central blood supply is gained, enabling for example delivery of drugs, infusion fluids or nutrition, along with the gathering of patient blood for blood gas analysis and the like.

In many patients, such as ICU patients, fever is a common occurrence. Fever is particularly likely in neuro-ICU patients, and its onset can exacerbate detrimental effects in the brain. Conventional therapies to control fever include treatment with acetaminophen (Tylenol™), ibuprofin, cooling blankets, ice water bladder lavages, and ice baths. All of these approaches to cooling a patient require excessive time to cool the patient. Moreover, prior methods do not provide for precise control of patient cooling. As recognized herein, to optimize the advantage of cooling a patient, it is important to cool the patient relatively quickly in a controlled fashion.

Recognizing the above-mentioned deleterious effects of fever in ICU patients and the insufficiencies of present temperature control methods and devices, the present assignee has disclosed, in co-pending patent application Ser. Nos. 09/133,813 and 09/063,984, indwelling catheters that can be implanted in the body of a patient to remove heat from the blood supply of the patient. The indwelling catheters of the above-referenced applications are disposed in a heat exchange relationship with the blood supply, and a coolant is circulated through the catheters in a closed loop. These catheters lower the temperature of body tissue and, as mentioned above, can thereby improve the patient's medical outcome.

As understood by the present invention, the advantages of the above-referenced cooling catheters can be implemented in a central venous catheter configuration. As mentioned above, central venous catheters are commonly used in many ICU patients, including neuro-ICU patients, and with these combined recognitions, the present invention understands that it would be advantageous to provide a central venous catheter with the additional capability of cooling a patient. In doing so, the present invention satisfies the goals both of conventional central venous catheters as well as providing a means for effectively and precisely managing patient temperature in a single device.

BRIEF SUMMARY OF THE INVENTION

The present invention overcomes the deficiencies of the prior art by providing a central venous line catheter adapted to actively exchange heat with the body of the patient to thereby raise or lower body temperature as required. The central venous line is provided with a heat exchange element disposed in heat exchange relationship with the blood of the patient. The heat exchange element houses a circulating fluid therein, with the fluid being automatically cooled or warmed exteriorly of the patient's body in accordance with a patient temperature feedback scheme.

By supplementing the known functions of a central venous line catheter with the function of cooling or warming the patient's blood, the present invention takes advantage of existing access to the venous system and a single incision, reducing the risk of additional complications. The access, typically through the subclavian, jugular or femoral veins, is to the central blood supply, via the central venous system, and is therefore particularly expedient, permitting efficient cooling or warming of patient body temperature. The term central venous system generally relates to the portion of the venous system which returns blood to the right heart, including the inferior and superior vena cava. A particular advantage of the invention is that the cooling function is performed efficiently in tandem with a procedure which is known to be likely attended by fever, thus anticipating such fever and facilitating its control. The heat exchange relationship between the system and the central venous system of the patient can be maintained for a prolonged duration—for example, from about one hour to about twenty-nine days.

The central venous line catheter in accordance with the invention comprises a tubular structure defining a plurality of lumens. At least two of these lumens convey heat exchange fluid to a heat exchange element disposed at a distal, implantable end of the central venous line catheter, while the rest of the lumens serve to provide access to the central blood supply of the patient. The heat exchange element is in fluid communication with a temperature control module via a tubing set which conveys the heat exchange fluid between the components. The temperature control unit, comprising a cooling and/or a heating device, operates in conjunction with a temperature controller to heat or cool the heat exchange fluid depending on a sensed temperature of the patient.

The system of the invention operates to maintain patient temperature at a desired level. Any deviation from the desired level automatically triggers corrective action, such as circulating the cooled heat exchange fluid through the central venous line catheter to contend with the onset of fever. Additionally, the system is equipped with indicators which signal to the caretaker of the patient the sensed deviation, by for example sensing the increased workload of the system, in order to warn of adverse physiological changes besetting the patient.

In accordance with one embodiment, the heat exchange element comprises a pair of axially arranged balloons which communicate with a corresponding lumens serving to supply heat exchange fluid for circulation in the balloons. The lumens and balloons are arranged such that a serial flow pattern between the balloons is established, and preferably, a pattern in which fluid flows from the distal balloon to the proximal balloon. In this manner heat exchange is optimized.

The invention thus provides a system for controlling patient temperature using a central venous line catheter having a heat exchange element. The central venous line catheter is provided with one or more lumens for providing access to the central blood supply of the patient, and with additional lumens for communicating heat exchange fluid to the heat exchange element. Heat exchange fluid temperature is controlled through a feed back loop in which patient temperature is sensed and used to control a temperature control unit comprising a heating device and/or a cooling device in heat exchange relationship with the heat exchange fluid. A tubing set transports the heat exchange fluid between the central venous line and the temperature control unit, with a pump serving to circulate the fluid in a closed fluid circuit in the system.

In accordance with the invention, patient body temperature can be therapeutically reduced by circulating a cooling fluid as the heat exchange fluid in a catheter in a patient-implanted catheter such as a central venous line catheter. Such an application can be attended by the use of warm blankets or other heating means to prevent a shivering response in the patient. Warm blankets will effectively keep the body's nerve receptors from triggering the shivering response, which would cause warming of the body and reduce the effects of the hypothermia-inducing procedure.

BRIEF DESCRIPTION OF THE SEVERAL VIEWS OF THE DRAWING(S)

Many advantages of the present invention will be apparent to those skilled in the art with a reading of this specification in conjunction with the attached drawings, wherein like reference numerals are applied to like elements and wherein:

FIG. 1 is a schematic diagram showing a central venous line catheter temperature control system in accordance with the present invention;

FIG. 2 is a schematic side elevational view of a central venous line catheter in accordance with the invention;

FIG. 3 is a schematic cross-sectional view taken along line 3—3 of FIG. 2;

FIG. 4 is a schematic cross-sectional view of a preferred arrangement of a catheter in accordance with the invention;

FIG. 5 is a schematic sectional view of the distal portion of the central venous line catheter of the invention;

FIG. 6 is a schematic side elevational view of a central venous line catheter in accordance with a second embodiment of the invention;

FIG. 7 is a schematic side elevational view of a central venous line catheter in accordance with a third embodiment of the invention;

FIG. 8 is a perspective view of one embodiment of the present anchor;

FIG. 9 is a side elevational cut-away view of dual balloon central venous line catheter in accordance with the invention;

FIG. 10 is a cross-sectional view as seen along the line 10—10 in FIG. 9; and

FIG. 11 is a plan view of the dual balloon central venous line temperature controller of the present invention, schematically showing central venous components.

DETAILED DESCRIPTION OF THE INVENTION

FIG. 1 shows a temperature control system 10 in accordance with the invention. A central venous line catheter 20 providing access to the central blood supply of the patient is disposed in heat exchange relationship with the patient. Central venous line catheter 20 is provided with a circulating heat exchange fluid (not shown) whose temperature is automatically controlled in accordance with a feedback scheme in order to achieve a desired patient target temperature or temperature range. The feedback scheme involves sensing patient temperature using a probe 54 whose output is provided to a temperature controller 55 housed in a temperature control module 50. The probe 54 can be a bladder probe, or rectal probe, or esophagus probe, or blood stream probe, or indeed can be an infrared tympanic temperature sensor. The temperature controller 55 determines whether the sensed temperature represents a deviation from the desired temperature or range and selectively activates a heat control unit 57 in order to heat or cool the heat exchange fluid depending on the direction of deviation. As described in more detail below, the central venous line catheter 20 is a multi-lumen device, with at least two of the lumens being dedicated to heat exchange fluid flow to and from a heat exchange element of the catheter. The other lumen(s) can have different uses, such as fluid infusion or drug delivery, or guidewire support or pressure monitoring, depending on the particular application. The preferred number of lumens is 3 to 5, although other numbers are contemplated.

FIGS. 2–5 show in more detail the central venous line catheter 20, which is a substantially elongate structure of generally cylindrical shape adapted for insertion into the body of a patient, preferably into the subclavian or jugular veins. Central venous line catheter 20 is formed of any known polymer material 23 defining its various lumens 32, 34, 42, 44 and 46. A preferred material is polyurethane, although other materials, such as nylon, polyester, silicone, polyethylene and PEBAX, can also be used. Considerations in selecting the appropriate material 23 include biocompatibility, flexibility, temperature change compatibility, and resistance to buckling.

At its distal, implantable end portion 22, catheter 20 is provided with a heat exchange element such as fluid-carrying inflatable balloon 24 that is radially disposed around the width of the catheter. Balloon 24 is disposed in the vicinity of flexible tip 21 and can be formed from a piece of sheet material 38 or extruded tubing formed into a molded balloon of the desired shape and size and then bound or otherwise fixed to the shaft 25 to form a cavity 36. As illustrated, balloon 24 is shown to have a significantly larger diameter than shaft portion 25 of the catheter. For example, it is contemplated that in some applications the diameter of the inflated balloon will be more than three times that of shaft 25. In one preferred embodiment, the balloon diameter is four millimeters to ten millimeters (4 mm–10 mm). Preferably, the diameter of the balloon is selected to be no more than 40%–60% of the diameter of a typical vena cava. It is to be appreciated that in some cases it may be desirable to maximize the dimension of the shaft 25 in order to facilitate heat exchange fluid flow. This will also minimize the volume of fluid in the balloon 24 and promote a more rapid heat exchange. It will be further appreciated that myriad balloon shapes can be utilized with the invention, including but not limited to spiral or fluted shapes, as disclosed in the aforementioned co-pending patent applications. Likewise, one balloon may be a different diameter than the other balloon(s). The particular shape selected would depend on the application and the desired heat exchange and other characteristics. In one preferred embodiment, the balloon 24 is made of urethane, nylon, or PET and is thin-walled, i.e., the balloon 24 has a wall thickness of less than three mils, and more preferably less than one and one-half mil. Also, the balloon 24 preferably is coated with an antimicrobial substance, as well as an anticlot substance, such as heparin.

It is to be understood that the balloon 24 can extend the entire length of the portion of the central venous catheter that is intubated in the patient. Typically, this length is about 15 cm. Under such circumstances, the diameter of the balloon need not be larger than the diameter of a conventional central venous catheter, e.g., the diameter of the balloon can be 12 French, 10 French, or even as small as 7.5 French. More broadly, the balloon diameter, when the balloon extends along the entire length of the intubated portion of the catheter, can be 5–15 French. In an arrangement where multiple balloons are used as detailed below, these balloons can cover the entire length of the intubated portion of the catheter. That is, two balloons of about 7.5 cm each can be used, or three 5 cm balloons, etc.

As can be seen more clearly with reference to FIGS. 3 and 4, a pair of lumens 32 and 34 are formed in catheter 20, with lumen 32 serving as an inflow channel supplying balloon 24 with heat exchange fluid which is circulated through the catheter 20, while lumen 34 serves as an outflow channel returning the heat exchange fluid from the balloon 24 to the catheter. The particular heat exchange fluid selected is preferably biocompatible to avoid harm to the patient in the event of inadvertent rupture. Candidate materials include sterile saline water and carbon dioxide gas, although other fluids having suitable viscosity, heat exchange and material compatibility characteristics can also be used. While less desired because it is not biocompatible, freon can alternatively be used.

Balloon 24 is in fluid communication with lumens 32 and 34 via a plurality of ports such as inlet port 26 and outlet port 28. Heat exchange fluid circulated in catheter 20 passes from lumen 32 into cavity 36 through inlet port 26, then out of cavity 36 to lumen 34 through outlet port 28. While in the cavity 36, the heat exchange fluid, which is remotely cooled outside the central venous line catheter 20, serves to provide a cold temperature fluid on the inner surface of the sheet material 38 which forms the walls of balloon 24. With a body fluid, such as blood, flowing exteriorly of the balloon 24, heat transfer occurs across the sheet material 38, effectively cooling the body of the patient and countering the effects of a fever. To that end, inlet port 26 is positioned distally of outlet port 28.

Efficient heat transfer is also promoted by specific considerations regarding the cross-sectional shape of the lumens 32 and 34. Specifically, as can be seen from FIG. 3, the lumens 32 and 34 are designed to maximize the volume of fluid flowing therethrough. This is accomplished by providing the lumens with crescent cross-sectional shapes so as to occupy circumferentially a maximum arc length in the catheter 20. This volume maximization, however, may be at the expense of thermal efficiency since the crescent cross-sectional shapes provide greater surface area for undesirable heat exchange with the exterior of the catheter 20 in the shaft portion 25.

In order to facilitate fluid flow in and out of cavity 36 of balloon 24, outlet port 28 can be made larger than inlet port 26 to reduce the resistance encountered by the heat exchange fluid as it exits the balloon 24. This relative size difference becomes particularly important when multiple balloons are provided in catheter 20 as is contemplated in accordance with an alternate embodiment of the invention. Specifically, although described in terms of a single balloon 24, it will be appreciated that several such balloons can be provided, disposed axially along the length of shaft 25, as shown in FIG. 6. One advantage of a multiple balloon configuration is that the flow and temperature of the heat exchange fluid can be more easily controlled along the entire length of the heat exchange region of the catheter 20. Realizing that the heat exchange fluid will be coolest prior to entering into heat exchange with the blood, and warmest after that heat exchange, one can advantageously control not only the velocity and volume of flow, but also the direction of flow within each of the balloons 24. Another advantage of a multiple balloon design is the ability of the catheter to bend and flex when placed in a curved vasculature.

Catheter 20 is also provided with two or three lumens 42, 44 and 46 in addition to lumens 32 and 34. Lumens 42, 44 and 46 can serve a multiplicity of functions, including pressure monitoring, infusion of drugs such as chemotherapy, fluids and nutrition, access to syringes for sampling, and accommodation of various sensors, such as thermistors to monitor the patient, thus generally providing access to the central blood supply as dictated by the particular application. Additionally, central lumen 44 may be made of a different diameter than side lumens 42 and 46 in order to better support a guidewire for instance. The lumens extend substantially the full length of catheter 20, from proximal end portion 27 to distal end portion 22. The number of lumens provided can be varied depending on the particular application.

It will also be appreciated that the heat exchange element does not necessarily need to be in the form of a balloon such as balloon 24. Rather, arrangements such as an array of flexible hollow fibers through which the heat exchange fluid is circulated can also be used, thus affording greater surface area for heat exchange interaction. Such an arrangement, along with other heat exchange element arrangements which can be used with the invention, is disclosed in the aforementioned co-pending patent application Ser. No. 09/133, 813, herein incorporated by reference in its entirety. A hollow fiber heat exchange element configuration is shown in FIG. 7. Hollow fibers 58 receive fluid from inner heat exchange fluid lumen 62 and return this fluid to outer heat exchange fluid lumen 64 of catheter 20. Additional lumens such as lumen 66 are also provided to facilitate delivery of fluids and for other uses. An important advantage of a hollow fiber heat exchange element arrangement is that it enables communication between the inner lumens, such as lumen 66, and the blood anywhere along the length of the heat exchange element, via for example port 68.

With reference again to FIG. 1, and in cross-reference to FIG. 2, the catheter 20 operates in conjunction with a temperature control module 50. A tubing set 52 (FIG. 1) engages coolant inlet and outlet fittings 52a, 52b on the catheter (FIG. 2) to convey fluid between temperature control module 50 and catheter 20 in a closed fluid circuit through which the fluid is circulated, using known pumping means (not shown) such as for example a diaphragm pump, bladder pump, piston pump, peristaltic pump, etc. It is to be understood that the inlet and outlet fittings 52a, 52b establish pathways of fluid communication from the temperature control unit 57 to the lumens 32, 34, respectively of the catheter 20. A temperature controller 55, which may be a microprocessor having appropriate information storage memory (not shown), is provided in temperature control module 50 and receives patient temperature signals from probe 54. By controlling the input to a temperature control unit 57, which may be a cooling device and/or a heating device in heat exchange relationship with the cooling fluid, temperature controller 55 automatically adjusts the temperature of the heat exchange fluid according to a desired target temperature or temperature range. The target temperature or range can be entered using an input device such as keyboard 56. A display device such as LCD 58 displays various parameters to provide indications of system operation and/or patient condition.

Preferably, the target temperature is selected to be normal body temperature, and any deviation from this temperature, for example induced by the onset of fever, is sensed by the probe 54 and automatically corrected by the system of the invention. Temperature correction is effected by for example activating temperature control unit 57 of temperature control module 50. In cooling applications, temperature control unit 57 causes cooling of the circulating fluid and ultimately the cooling of the patient's core body temperature, which is monitored by probe 54. When normal temperature is achieved, the temperature control unit 57 can then be automatically switched off or its cooling effect reduced by the temperature controller 55. Suitable temperature control algorithms taking into account performance parameters of system components and system time constants are implemented by temperature controller 55 to effect accurate temperature control. For more expedient temperature control, module 50 may also be provided with a heating device as part of the temperature control unit 57, which heating device can also be automatically activated, using feedback from probe 54, to for example prevent overshooting the desired target temperature or range to re-warm the patient, or even to induce hyperthermia in some situations. As mentioned above, it will be appreciated that probe 54 can be used to provide temperature feedback from any part of the patient's body, rectally for instance, or it can provide temperature information anywhere in the fluid circuit, which information can then be correlated to the patient's core temperature using known parameters such as heat conductivity of different portions of the system and patient data such as weight, height, age, etc. Additionally, more than one probe can be used to provide combinations of readings from the patient and/or from the system to improve accuracy under some circumstances.

In accordance with the invention, the feedback scheme can be used to maintain desired temperature conditions for a patient. Specifically, the system can be used to control any temperature deviations from an acceptable temperature range, which may be a normothermic range, whereby probe 54 will trigger cooling or heating of the patient's body depending on this sensed deviation from the predetermined range. Moreover, since this deviation is generally indicative of certain physiological activity of which the patient's caretaker should be apprised, the operation of the system can be used as an indication that this physiological activity is taking place. For instance, when the cooling operation of temperature control unit 57 is activated due to a rise in the patient's core body temperature, the system cooling activity, as reflected in the increased workload of the cooling componentry of the system, is then used to indicate to the caretaker, audibly or visibly using an alarm or other status indicator device (not shown) for instance, that the patient's body is attempting to enter a fever state. Appropriate measures can then be taken. Parameters other than workload can be used to provide this indication, such as the slope of the temperature feedback along with the sign of the slope. Alternatively, a direct indication of patient temperature as sensed by the probe 54 can be used. In this manner, use of the system for extended periods of time—for example, from about one hour to about twenty-nine or more days—is facilitated.

In cross-reference to FIGS. 1 and 2, in addition to being connected to the temperature control unit 50, the central venous catheter 20 is connected to one or more central venous components 70, 72 (only two venous components shown in FIG. 1 for clarity of disclosure) via respective fittings 74, 76, 78 as appropriate (FIG. 2) to establish communication between the central venous components 70, 72 and selected lumens 42, 44, 46 of the catheter 20. As intended by the present invention, the central venous components 70, 72 can be established by one or more of: drug infusion sources, blood receptacles for receiving blood through the catheter 20, a guide wire, etc.

Additionally, as best seen in FIG. 2, the catheter 20 includes an anchor configured for affixing the catheter 20 to the patient. More specifically, in one intended embodiment, the anchor is established by a suture fitting 80. The suture fitting 80 can be made integrally with the catheter 20, or it can be made as a separate plastic fitting and slidably engaged with the catheter 20. As shown, the suture fitting 80 includes two eyes 82, 84 through which sutures can be positioned and engaged with the patient's skin or with a bandage or tape or other structure that has been fastened to the patient. Alternatively, the present anchor can be established by a piece of tape 86, shown in FIG. 8, that can tape the catheter of the present invention to the patient. Yet again, the present anchor can include another fastening device such as a plate with adhesive surface that can be engaged with the patient, with the plate including structure configured for receiving the catheter of the present invention, or the anchor can be a suture ring. As understood herein, an anchor is desirable in a central venous catheter to hold the catheter on the patient, because a central venous catheter typically is intended for prolonged indwelling.

FIGS. 9–11 show an exemplary embodiment in which a pair of balloons are used to effect the heat exchange. Proximal balloon 102 and distal balloon 104 are disposed axially along catheter 100 and are designed to contain heat exchange fluid circulated therein. In a preferred embodiment, the outer diameter (when inflated) of the distal balloon 104 can be the same as or somewhat larger than the outer diameter (when inflated) of the proximal balloon 102. For example, the distal balloon can have an inflated outer diameter of five millimeters and the proximal balloon can have an inflated outer diameter of four millimeters. Additionally, the balloons 102, 104 are preferably made of polyurethane made by Zynergy Core Technology, Inc. and having a wall thickness of from one-half mil to one mil. The particularly preferred material can be Zynergy model Z51A or Z111A, and can have a hardness of at least 75 Shore D. Accordingly, the comparatively thin-walled yet strong balloons 102, 104 facilitate heat transfer.

Distal balloon 104 is in fluid communication with a supply lumen 106, via a relatively distal inlet port 110, and is in fluid communication with a segment 108a of a return lumen 108, via a relatively proximal outlet port 112. Proximal balloon 102 is in fluid communication with segment 108a of return lumen 108 via a relatively distal inlet port 114, and with return lumen 108 via relatively proximal outlet port 116. Thus, the heat exchange fluid flow direction through balloons 102, 104 is from distal to proximal, as further explained below. Lumens 106 and 108 are in communication with a heat exchange fluid source, such as temperature control module 50, in the manner described above, as can be seen from FIG. 11. For this purpose, lumens 106 and 108 communicate with tubes 122 and 120, respectively, and with fittings 124 and 126, respectively, to achieve the proper connections. A fluid circuit is thus established which includes temperature control module 50, tubes 120 and 122, lumens 106 and 108, and balloons 102 and 104. The circuit contains a heat exchange fluid circulated therein to thereby effect automatic temperature control of the patient consistent with the description of the invention provided above.

An occlusion 118 is disposed in lumen 108 to thereby demarcate segment 108a of return lumen 108. Occlusion 118 prevents direct fluid flow between segment 108a and the remainder of the return lumen 108. Instead, fluid flow from segment 108a is diverted into proximal balloon 102 before returning to lumen 108 proper. In this manner segment 108a provides an intermediate fluid flow pathway between distal balloon 104 and proximal balloon 102 and serves as the exclusive fluid flow path between the balloons. The arrows in FIG. 9 indicate the direction of heat exchange fluid flow during operation.

In accordance with the arrangement of FIGS. 9–11, a serial flow of heat exchange fluid through balloons 102 and 104 is established. The serial flow configuration provides improved heat exchange characteristics over parallel flow because the fluid flow is not divided among the two balloons. The heat exchange characteristics are improved further still by ensuring a reverse flow pattern characterized by the flow of the heat exchange fluid from the distal balloon 104 to the proximal balloon 102, and even more specifically, from the distal end of distal balloon 104, to the proximal end of distal balloon 104, then from the distal end of the proximal balloon 102, to the proximal end of the proximal balloon 102. Although this reverse flow pattern relative to the direction of blood flow in the vessel is preferred, it is contemplated that a forward flow pattern can be deployed, with fluid flowing serially from the proximal balloon to the distal balloon.

As shown best in FIG. 10, two access lumens 128 and 130 run axially along the length of the catheter. Access lumens 128 and 130 provide access, via the catheter 100, to the patient's central venous system from a remote exterior location. CV components 132 and 134 are shown as gaining such access through tubes 136 and 138 and lumens 128 and 130 in communication therewith. Examples of CV components which can be accommodated include, but are not limited to: syringes or other delivery devices for delivering drugs, nutrition or other fluids or material; blood extraction devices; and blood monitoring devices. Of course, the number of access lumens such as lumens 128 and 130 can be more than or less than two, depending on the particular application, and the access provided thereby can be to any number of CV components.

Tubes 136, 138 are relatively more compressible than coolant tubes 120, 122, because coolant tubes 120, 122 are not intended to be clamped whereas tubes 136, 138 might require clamping with clamp 137 in accordance with central venous access principles. This difference in compressibility can be achieved by making the walls of tubes 120, 122 thicker than the walls of tubes 136, 138 and/or by making the tubes 120, 122 of higher durometer than tubes 136, 138, i.e. 120, 122 with walls 0.018" thick and 100A durometer 136, 138 with walls 0.015" and 93A durometer.

An important feature of the dual balloon arrangement of FIGS. 9–11 is that the termini of the access lumens can be axially offset along the catheter 100. As shown in FIG. 11, the terminus of access lumen 128 is shown to be an access port 140, while the terminus of access lumen 130 is shown to be at an access port 142. Access port 142 is located at distal tip 144 of catheter 100. Access port 140, on the other hand, is located in a region intermediate to distal balloon 104 and proximal balloon 102. Advantages of such an arrangement include the ability to infuse drugs that are potentially incompatible to each other into the central venous system of the patient. Because of the spacing between access ports 140 and 142, mixing of such incompatible drugs as they are introduced into the patient's blood stream is minimized. Furthermore, because two relatively short balloons are used instead of one longer balloon, and the proximal-most port 140 is established between the balloons, the proximal port 140 is placed deeper into the venous system than it would be were it located proximal to a single long balloon, thus reducing the possibility of caustic effects to the vessel wall that might otherwise occur were drugs to be infused from a port that was proximal to a single long balloon and, thus, relatively close to the entry point of the device.

The teachings of the present invention can be applied for therapeutically inducing hypothermia in a patient, by circulating a cooling fluid as the heat exchange fluid in the catheter to thereby reduce patient temperature. Such an application can be attended by the use of warm blankets or other heating means to prevent a shivering response in the patient. Warm blankets will effectively keep the body's nerve receptors from triggering the shivering response, which would cause warming of the body and reduce the effects of the hypothermia-inducing procedure.

The above are exemplary modes of carrying out the invention and are not intended to be limiting. It will be apparent to one of ordinary skill in the art that modifications thereto can be made without departure from the spirit and scope of the invention as set forth in the following claims.

What is claimed is:

1. A heat exchange catheter comprising:
    a catheter body having at least a heat exchange fluid supply lumen and a heat exchange fluid return lumen; and
    at least a distal balloon and a proximal balloon on the catheter body, the balloons and lumens being arranged such that heat exchange fluid flows serially through the balloons.

2. The catheter of claim 1, further comprising an intermediate fluid pathway between the distal and proximal balloons and a heat exchange fluid inlet port formed in the supply lumen, the inlet port allowing heat exchange fluid to flow into the distal balloon and intermediate fluid pathway.

3. The catheter of claim 2, further comprising an occlusion in the heat exchange fluid return lumen, the occlusion causing heat exchange fluid to flow from the distal balloon into the proximal balloon.

4. The catheter of claim 1, further comprising first and second access lumens terminating in respective first and second access ports communicating with the exterior of the catheter, the access ports being axially spaced from each other.

5. The catheter of claim 4, wherein the catheter is provided with a distal tip, the first access port being disposed at the distal tip and the second access port being disposed between the distal and proximal balloons.

6. A central venous line catheter comprising:
    a substantially elongate structure configured for establishing venous access, said structure having a proximal portion and a distal portion and defining at least a first access lumen in communication with the exterior of the structure at said proximal and distal portions;
    a proximal and a distal balloon disposed axially along the substantially elongate structure, the proximal and distal balloons adapted to effect heat exchange with the central venous system;
    a heat exchange fluid supply lumen in fluid communication with the distal balloon;
    a heat exchange fluid return lumen in fluid communication with the proximal balloon;
    wherein a serial fluid flow path is established from the distal balloon to the proximal balloon such that fluid flows from the supply lumen, to the distal balloon, a segment of the return lumen, then to the proximal balloon, then to the remainder of a return lumen.

7. The catheter of claim 6, further comprising an occlusion for preventing fluid flow between the segment of the return lumen and the remainder of the return lumen.

8. The catheter of claim 6, further comprising a second access lumen in communication with the exterior of the structure at said proximal and distal portions.

9. The catheter of claim 8, wherein the first and second access lumens are in fluid communication with the exterior of the substantially elongate structure at respective first and second access ports, the first access port being disposed distally of the distal balloon and the second access port being disposed proximally of the distal balloon.

10. The catheter of claim 9, wherein the second access port is disposed distally of the proximal balloon.

11. A patient temperature control system comprising:
a central venous line catheter having a proximal portion and a distal portion and defining at least a first access lumen in communication with the exterior of the catheter at the proximal and distal portions;
a proximal and a distal balloon disposed axially along the central venous line catheter, the proximal and distal balloons adapted to effect heat exchange with the central venous system;
a heat exchange fluid supply lumen in fluid communication with the distal balloon;
a heat exchange fluid return lumen in fluid communication with the proximal balloon; and
a temperature control unit for providing heat exchange fluid to the heat exchange fluid supply lumen and for receiving heat exchange fluid from the heat exchange fluid return lumen, the heat exchange control unit adapted to change the temperature of a heat exchange fluid circulated in the proximal and distal balloons,
wherein a serial fluid flow path is established between the proximal and distal balloons.

12. The patient temperature control system of claim 11, further comprising at least one probe for sensing patient temperature, the temperature control unit automatically changing the temperature of the heat exchange fluid in accordance with the sensed patient temperature.

13. The patient temperature control system of claim 12, further comprising a temperature controller for activating the temperature control unit when patient temperature deviates from a predetermined range.

14. The patient temperature control system of claim 12, wherein the temperature control unit comprises at least one cooling device for cooling the heat exchange fluid.

15. The patient temperature control system of claim 12, wherein the temperature control unit comprises at least one heating device for heating the heat exchange fluid.

16. The patient temperature control system of claim 11, further comprising at least one tubing set in fluid communication with the heat exchange fluid supply and return lumens and the temperature control unit, the tubing set delivering fluid between the central venous line catheter and the temperature control unit.

17. The patient temperature control system of claim 11, further comprising means for providing an indication of patient temperature change.

18. The patient temperature control system of claim 11, further comprising at least one central venous line catheter anchor engaged with the catheter and including structure configured to affix the catheter to the patient.

19. The patient temperature control system of claim 11, wherein a serial fluid flow path is established from the distal balloon to the proximal balloon such that fluid flows from the supply lumen, to the distal balloon, then to a segment of the return lumen, then to the proximal balloon, then to the remainder of a return lumen.

20. The catheter of claim 19, further comprising an occlusion for preventing fluid flow between the segment of the return lumen and the remainder of the return lumen.

21. The catheter of claim 11, further comprising a second access lumen in communication with the exterior of the central venous line catheter at said proximal and distal portions.

22. The catheter of claim 21, wherein the first and second access lumens are in fluid communication with the exterior of the central venous line catheter at respective first and second access ports, the first access port being disposed distally of the distal balloon and the second access port being disposed proximally of the distal balloon.

23. The catheter of claim 22 wherein the second access port is disposed distally of the proximal balloon.

24. A heat exchange catheter comprising:
a catheter body having at least one heat exchange fluid supply lumen and at least one heat exchange fluid return lumen;
a first coolant tube in communication with said fluid supply lumen;
a second coolant tube in communication with said fluid return lumen;
at least two balloons on said catheter body, said balloons and said fluid supply lumen and said fluid return lumen being arranged such that heat exchange fluid flows serially through said balloons;
at least one infusing tube connected to said catheter body; and
a clamp engaged with said infusing tube, said clamp for selectively blocking fluid flow through said infusing tube.

25. The heat exchange catheter of claim 24 wherein said coolant tubes are constructed from a first material, and said infusing tube is constructed from a second material being more compressible than said first material.

26. The heat exchange catheter of claim 24 wherein:
said coolant tubes further comprises coolant tubing walls;
said infusing tube further comprises infusing tubing walls; and
said coolant tubing walls are thicker than said infusing tubing walls.

27. A heat exchange catheter comprising:
a catheter body having at least one heat exchange fluid supply lumen and at least one heat exchange return lumen;
a first coolant tube in communication with said fluid supply lumen, said first coolant tube being constructed of a first material;
a second coolant tube in communication with said return lumen, said second coolant tube being constructed of said first material;
at least two balloons on the catheter body, said balloons and said fluid supply lumen and said return lumen being arranged such that heat exchange fluid flows serially through said balloons; and
at least one infusing tube connected to said catheter body, said infusing tube is constructed of a second material being more compressible than said first material.

28. The heat exchange catheter of claim 27 further comprises a clamp in communication with said infusing tube, said clamp for selectively blocking fluid flow through said infusing tube.

29. The heat exchange catheter of claim 27 wherein said first material is thicker than said second material.

30. The heat exchange catheter of claim 27 wherein said catheter body further comprises at least one balloon, said balloon communicating with said coolant tubes.

* * * * *